(12) United States Patent
Berrevoets et al.

(10) Patent No.: US 8,414,616 B2
(45) Date of Patent: Apr. 9, 2013

(54) MOUNTING DEVICES FOR FIXATION DEVICES AND INSERTION INSTRUMENTS USED THEREWITH

(75) Inventors: Gregory Berrevoets, Skandia, MI (US); Maria Norman, Negaunee, MI (US); Brad Fredin, Negaunee, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 740 days.

(21) Appl. No.: 11/854,393

(22) Filed: Sep. 12, 2007

(65) Prior Publication Data

US 2008/0108997 A1 May 8, 2008

Related U.S. Application Data

(60) Provisional application No. 60/825,384, filed on Sep. 12, 2006.

(51) Int. Cl.
*A61B 17/70* (2006.01)

(52) U.S. Cl. .......................................... 606/250; 606/297

(58) Field of Classification Search ............... 606/70–71, 606/78, 246–299, 903–906; 408/223–232
See application file for complete search history.

(56) References Cited

U.S. PATENT DOCUMENTS

| | | | |
|---|---|---|---|
| 284,118 A | 8/1883 | Cilley | |
| 463,785 A | 11/1891 | Connable et al. | |
| 836,217 A | 11/1906 | Rowe | |
| 1,816,446 A | 7/1931 | Stapf | |
| 2,500,370 A | 3/1950 | McKibbin | |
| 2,670,519 A | 3/1954 | Recklitis | |
| 3,870,048 A | 3/1975 | Yoon | |
| 3,920,350 A * | 11/1975 | Southall | 408/211 |
| 4,047,524 A * | 9/1977 | Hall | 606/75 |
| 4,174,715 A | 11/1979 | Hasson | |
| 4,278,091 A | 7/1981 | Borzone | |
| 4,374,523 A | 2/1983 | Yoon | |
| 4,566,466 A | 1/1986 | Ripple et al. | |
| 4,896,678 A | 1/1990 | Ogawa | |
| 4,960,420 A | 10/1990 | Goble et al. | |
| 4,994,079 A | 2/1991 | Genese et al. | |
| 5,147,361 A | 9/1992 | Ojima et al. | |
| 5,222,973 A | 6/1993 | Sharpe et al. | |
| 5,238,002 A | 8/1993 | Devlin et al. | |
| 5,258,005 A | 11/1993 | Christian | |
| 5,271,385 A | 12/1993 | Bailey | |

(Continued)

FOREIGN PATENT DOCUMENTS

| | | |
|---|---|---|
| DE | 735333 | 5/1943 |
| DE | 4114311 | 11/1992 |

(Continued)

*Primary Examiner* — Kevin T Truong
*Assistant Examiner* — Larry E Waggle, Jr.
(74) *Attorney, Agent, or Firm* — Fitch, Even, Tabin & Flannery LLP

(57) ABSTRACT

A vertebral cleat and a vertebral support system employing the vertebral cleat is provided. Preferably, the vertebral cleat includes a base member having a superior and an inferior surface; an elongate keel portion having a cutting edge thereon depending from the inferior surface of the base member; and a spike portion depending from the inferior surface of the base member, the spike portion having a height that is greater than a height of the elongate keel portion. There is also provided a tool for grasping and implanting the vertebral cleat in a plurality of insertion configurations.

9 Claims, 17 Drawing Sheets

U.S. PATENT DOCUMENTS

| | | |
|---|---|---|
| 5,284,162 A | 2/1994 | Wilk |
| 5,318,589 A | 6/1994 | Lichtman |
| 5,352,229 A | 10/1994 | Goble et al. |
| 5,395,372 A * | 3/1995 | Holt et al. .................... 606/86 B |
| 5,407,243 A | 4/1995 | Riemann |
| 5,562,736 A | 10/1996 | Ray et al. |
| 5,569,262 A | 10/1996 | Carney |
| 5,603,723 A | 2/1997 | Aranyi et al. |
| 5,616,144 A | 4/1997 | Yapp et al. |
| 5,618,304 A | 4/1997 | Hart et al. |
| 5,636,639 A | 6/1997 | Turturro et al. |
| 5,690,629 A * | 11/1997 | Asher et al. .................... 606/265 |
| 5,728,127 A | 3/1998 | Asher et al. |
| D394,663 S * | 5/1998 | Stone et al. .................... D15/139 |
| 6,045,552 A * | 4/2000 | Zucherman et al. ........ 606/86 B |
| 6,066,174 A | 5/2000 | Farris |
| 6,099,550 A | 8/2000 | Yoon |
| 6,136,002 A * | 10/2000 | Shih et al. .................... 606/250 |
| 6,159,162 A | 12/2000 | Kostylev et al. |
| 6,187,026 B1 | 2/2001 | Devlin et al. |
| 6,319,257 B1 | 11/2001 | Carignan et al. |
| 6,524,311 B2 * | 2/2003 | Gaines, Jr. .................... 606/278 |
| 6,533,787 B1 | 3/2003 | Lenke et al. |
| 6,602,257 B1 | 8/2003 | Thramann |
| 6,607,559 B2 | 8/2003 | Ralph et al. |
| 6,616,683 B1 | 9/2003 | Toth et al. |
| 6,669,730 B2 | 12/2003 | Ralph et al. |
| 6,673,113 B2 | 1/2004 | Ralph et al. |
| 6,733,504 B2 | 5/2004 | Lin et al. |
| 6,746,450 B1 * | 6/2004 | Wall et al. .................... 606/280 |
| 6,773,437 B2 | 8/2004 | Ogilvie et al. |
| 6,824,565 B2 | 11/2004 | Muhanna et al. |
| 6,830,571 B2 | 12/2004 | Lenke et al. |
| 6,860,889 B2 | 3/2005 | Bonati et al. |
| 6,863,689 B2 | 3/2005 | Ralph et al. |
| 6,902,566 B2 | 6/2005 | Zucherman et al. |
| 6,923,814 B1 | 8/2005 | Hildebrand et al. |
| 6,945,984 B2 | 9/2005 | Arumi et al. |
| 2001/0010000 A1 * | 7/2001 | Gertzbein et al. ............... 606/61 |
| 2002/0065560 A1 | 5/2002 | Varga et al. |
| 2002/0111683 A1 | 8/2002 | Ralph et al. |
| 2002/0111687 A1 | 8/2002 | Ralph et al. |
| 2002/0151979 A1 | 10/2002 | Lambrecht et al. |
| 2003/0009227 A1 | 1/2003 | Lambrecht et al. |
| 2003/0014113 A1 | 1/2003 | Ralph et al. |
| 2003/0014115 A1 | 1/2003 | Ralph et al. |
| 2003/0040802 A1 | 2/2003 | Errico et al. |
| 2003/0069586 A1 | 4/2003 | Errico et al. |
| 2003/0069592 A1 | 4/2003 | Adams et al. |
| 2003/0069642 A1 | 4/2003 | Ralph et al. |
| 2003/0069643 A1 | 4/2003 | Ralph et al. |
| 2003/0078590 A1 | 4/2003 | Errico et al. |
| 2003/0078662 A1 | 4/2003 | Ralph et al. |
| 2003/0083747 A1 | 5/2003 | Winterbottom et al. |
| 2003/0093155 A1 | 5/2003 | Lambrecht et al. |
| 2003/0130667 A1 | 7/2003 | Lin |
| 2003/0135275 A1 | 7/2003 | Garcia et al. |
| 2003/0149438 A1 | 8/2003 | Nichols et al. |
| 2003/0187454 A1 | 10/2003 | Gill et al. |
| 2003/0204362 A1 | 10/2003 | Beresford et al. |
| 2003/0216810 A1 | 11/2003 | Ralph et al. |
| 2003/0229358 A1 | 12/2003 | Errico et al. |
| 2004/0010316 A1 | 1/2004 | William et al. |
| 2004/0024462 A1 | 2/2004 | Ferree et al. |
| 2004/0030387 A1 * | 2/2004 | Landry et al. ............... 623/16.11 |
| 2004/0030390 A1 | 2/2004 | Ferree |
| 2004/0030391 A1 | 2/2004 | Ferree |
| 2004/0034426 A1 | 2/2004 | Errico et al. |
| 2004/0049280 A1 | 3/2004 | Cauthen |
| 2004/0068321 A1 | 4/2004 | Ferree |
| 2004/0093088 A1 | 5/2004 | Ralph et al. |
| 2004/0098129 A1 | 5/2004 | Lin |
| 2004/0127902 A1 * | 7/2004 | Suzuki et al. .................... 606/69 |
| 2004/0133132 A1 | 7/2004 | Chappuis |
| 2004/0133205 A1 | 7/2004 | Thramman et al. |
| 2004/0133278 A1 | 7/2004 | Marino et al. |
| 2004/0133280 A1 | 7/2004 | Trieu |
| 2004/0138662 A1 | 7/2004 | Landry et al. |
| 2004/0138701 A1 | 7/2004 | Haluck |
| 2004/0143331 A1 | 7/2004 | Errico et al. |
| 2004/0143332 A1 | 7/2004 | Krueger et al. |
| 2004/0148027 A1 | 7/2004 | Errico et al. |
| 2004/0148028 A1 | 7/2004 | Ferree et al. |
| 2004/0153158 A1 | 8/2004 | Errico et al. |
| 2004/0153159 A1 | 8/2004 | Cauthen |
| 2004/0162558 A1 * | 8/2004 | Hegde et al. .................... 606/61 |
| 2004/0167534 A1 | 8/2004 | Errico et al. |
| 2004/0167535 A1 | 8/2004 | Errico et al. |
| 2004/0167626 A1 | 8/2004 | Geremakis et al. |
| 2004/0167628 A1 | 8/2004 | Foley |
| 2004/0176843 A1 | 9/2004 | Zubok et al. |
| 2004/0176845 A1 | 9/2004 | Zubok et al. |
| 2004/0176848 A1 | 9/2004 | Zubok et al. |
| 2004/0186577 A1 | 9/2004 | Ferree |
| 2004/0220569 A1 | 11/2004 | Wall et al. |
| 2004/0225295 A1 | 11/2004 | Zubok et al. |
| 2004/0236333 A1 * | 11/2004 | Lin .................... 606/69 |
| 2004/0267275 A1 | 12/2004 | Cournoyer et al. |
| 2005/0027360 A1 | 2/2005 | Webb et al. |
| 2005/0033305 A1 | 2/2005 | Schultz |
| 2005/0033437 A1 | 2/2005 | Bao et al. |
| 2005/0033438 A1 | 2/2005 | Schultz et al. |
| 2005/0038445 A1 | 2/2005 | Errico et al. |
| 2005/0038515 A1 | 2/2005 | Kunzler |
| 2005/0038516 A1 | 2/2005 | Spoonamore |
| 2005/0055097 A1 | 3/2005 | Grunberg et al. |
| 2005/0060035 A1 | 3/2005 | Errico et al. |
| 2005/0071012 A1 | 3/2005 | Serhan et al. |
| 2005/0085917 A1 | 4/2005 | Marnay et al. |
| 2005/0113842 A1 | 5/2005 | Bertagnoli et al. |
| 2005/0119752 A1 | 6/2005 | Williams et al. |
| 2005/0131541 A1 | 6/2005 | Trieu |
| 2005/0143749 A1 | 6/2005 | Zalenski et al. |
| 2005/0143820 A1 | 6/2005 | Zucherman et al. |
| 2005/0143824 A1 | 6/2005 | Richelsoph et al. |
| 2005/0154463 A1 | 7/2005 | Trieu |
| 2005/0154464 A1 | 7/2005 | Humphreys et al. |
| 2005/0154466 A1 | 7/2005 | Humphreys et al. |
| 2005/0154468 A1 | 7/2005 | Rivin |
| 2005/0192670 A1 | 9/2005 | Zubok et al. |
| 2005/0192671 A1 | 9/2005 | Bao et al. |
| 2005/0203538 A1 | 9/2005 | Lo et al. |
| 2006/0030851 A1 | 2/2006 | Bray et al. |
| 2006/0036250 A1 | 2/2006 | Lange et al. |
| 2007/0191850 A1 * | 8/2007 | Kim et al. .................... 606/75 |

FOREIGN PATENT DOCUMENTS

| | | |
|---|---|---|
| EP | 598573 | 5/1994 |
| SU | 427703 | 5/1974 |
| SU | 1502020 | 8/1989 |
| WO | 9100713 | 1/1991 |
| WO | 9320759 | 10/1993 |
| WO | WO 03096914 A1 * | 11/2003 |
| WO | 04000177 | 12/2003 |
| WO | 2006025921 | 3/2006 |

* cited by examiner

MOUNTING DEVICES FOR FIXATION DEVICES AND INSERTION INSTRUMENTS USED THEREWITH

FIELD OF THE INVENTION

The invention relates to bone implants, and in particular, to mounting devices for providing a stable base for bone implant anchor members.

BACKGROUND OF THE INVENTION

Bone fixation devices are used in orthopedic surgery to align or fix a predetermined relationship between adjacent bones. One particular use for bone fixation devices is the fixation and alignment of adjacent vertebral bodies. These fixation devices commonly include an elongate rod to set the vertebrae into a desired alignment and various anchoring devices, such as hooks, bolts, wires, screws, and the like that secure the rods to the bone.

A common vertebral fixation device employs a rod and screw system. These systems may include plates that are attached to adjacent vertebrae desired to be fixed in order to provide a mounting base for the fixation device on each vertebra. A bone screw may then be inserted through openings in each mounting plate and screwed into each adjacent bone. To fix the position of the vertebrae, a spinal rod is oriented to extend between the fixation devices and is secured to the bone screws by lockable connecting members.

The mounting plate is advantageously employed to impair or minimize toggling of the bone screws when the rod and screws are subjected to a load. Severe or constant toggling of the bone screws can weaken the attachment to the bone, which may require replacement of the fixation device. Current mounting devices are in the form of staples that include multiple, narrow and discrete spikes that are driven into the bone. Generally, these prong or spike projections have depending shanks with a generally cylindrical, curved, or otherwise relatively small-sized peripheral surface having narrow flats that extend from the staple to pointed or sharp-edged ends for penetrating the bone material. These peripheral surfaces only present a small or curved surface area in confronting relation to adjacent bone material. The confronting surface portions, be they curved or flat, offer very little in the way of resistance thereto. Accordingly, subjecting these small sized shank surfaces to extensive cyclic loading such as when attached to vertebrae in a vertebral fixation device generally will cause weakening of the connection to the vertebral surface and over time cause loosening and play to develop at the interface between the surfaces and bone material. With loose play at the staple, there is the undesirable potential that the bone screw will be able to shift and toggle with loading applied thereto.

Most current vertebral staples having multiple spikes also have a shortcoming in that they generally do not allow the position of the staple to be adjusted after the staple is implanted into the bone. If first implanted in an incorrect position, the staple must be removed and re-inserted. A vertebral staple disclosed in WO 2006/025921 attempts to overcome this shortcoming by having shorter perimeter spikes and a longer, central spike. The shorter perimeter spikes allow rotation of the staple body when the longer central spike is only partially driven into the bone along a small end portion of its length. Therefore, such rotation permits final positioning of the screw openings of the spike prior to the final insertion where both the long and short spikes are driven into the bone.

While the staple of the '921 publication addresses the positioning shortcomings of other vertebral staples, this staple still employs several discrete spikes having relatively small periphery extending about the shanks. The narrow bone confronting surface portions of the perimeter and central spikes of the staple in the '921 publication still exhibit the same shortcomings of other vertebral staples where movement of the plate over time is more likely when experiencing repeated loads.

Accordingly, there is a need for a mounting device for use in a bone fixation system that allows pre-positioning of the implant prior to final implantation, and provides a stable mounting base for the fixation system.

SUMMARY OF THE INVENTION

In one aspect of the invention, a mounting device is provided that is arranged and configured for mounting to a bone in order to support anchor members, such as bone screws of a vertebral stabilizing system. Preferably, the mounting device is in the form of a vertebral cleat that is configured for mounting to a vertebral bone as part of a stabilization system to fix adjacent vertebrae together relative to each other.

In one form, the mounting cleat includes a bone securing member having an elongate keel portion with a relatively large surface area that resides in confronting relation to bone material with the keel driven therein for minimizing weakening of the keel/bone interface that may be experienced when under load. Accordingly, the keel minimizes the potential for toggling and movement over time when the anchor member and mounting device are subjected to repeated or cyclic loading. Preferably, the elongate keel has opposite elongate flat surfaces depending from the relatively flat body of the cleat. When the keel is driven into the vertebral bone, these long flat surfaces provide a large surface area that confronts and engages adjacent bone material. The present cleat is an enhanced mounting base over prior art staples because the keel provides increased resistance to toggling over that provided by the spikes of prior art staples with only relatively small or narrow bone confronting surface portions thereof.

The securing member having the relatively large bone contact area depends from an inferior surface of the mounting device, and preferably includes at least one depending spike portion and the elongate keel portion. To provide for insertion into a pre-position configuration, the keel extends for a distance transverse to and depending from the plate body of the cleat that is less than the length of the spike. The securing member, therefore, permits ease of positioning during implantation because the shorter keel allows rotation of the mounting device relative to a bone surface after initial positioning of the longer spike. That is, after an initial insertion of the mounting device where the longer spike is partially driven into the bone for only a short length of the end portion thereof and the shorter elongate keel is not driven into the bone, the mounting device will be substantially free to rotate about the spike. In this manner, a surgeon can more easily orient the mounting device into a desired final mounting position on the bone because the device is partially fixed to the bone through the spike, yet still adjustable via rotation about the spike. When the screw opening or openings are correctly positioned relative to the bone in the final mounting position, both the spike and keel are substantially fully driven into the bone.

A variety of configurations for the mounting device are possible, each having one or more openings for receiving bone screws and one or more securing members in the form of keels and/or spikes depending from its inferior surface. For instance, the mounting device may have a plurality of elongate keels depending therefrom. In one form, each of the plurality of keels contains a projection portion to more easily pierce through bone. The projection portion may be located anywhere along the length of the keel, for instance in the center or either end of the keel. The projection portion may be formed as a discrete spike projecting from the keel, or may be formed by a sloping or curving of the cutting edge of the keel. In another form, only some of the keels contain a projection portion. In still another embodiment, only one of a plurality of keels contains a projection portion. In yet another embodiment, only one elongate keel with one spike or projection portion depends from the body of the mounting device.

An insertion instrument for application of the mounting device is also provided. The instrument is adapted and configured to grasp the mounting device as the bone securing member or a portion thereof is driven into a vertebral bone. For example, the instrument may releasably hold the device as it is driven into the bone in both the partial and full insertion positions described above. A preferred instrument includes a gripping portion that is configured to hold the mounting device and an actuator portion that is operable to manipulate the gripping portion to grasp and release the mounting device as needed.

Because the mounting device is preferably contoured to match the shape of the bone outer surface, grasping any of the major surfaces of the mounting devices is often difficult due to the curvature of the surfaces to be grasped. Accordingly, the insertion instruments herein are configured to grasp a perimeter edge of the mounting device. To this end, the instrument includes an elongate sleeve or tube that defines a central bore and longitudinal axis extending therethrough. An elongate grasping fork is received within the bore and configured to slide along the longitudinal axis. Operation of an actuator causes the grasping fork to slide along the longitudinal axis within the bore so that a forked portion outside of the bore is operatable to grasp the perimeter edges of the mounting device rather than any of the major surfaces thereof. In this manner, the surgeon can easily manipulate the mounting device into the initial and final positions as described above.

DETAILED DESCRIPTION OF THE PREFERRED EMBODIMENT

Figure 1:
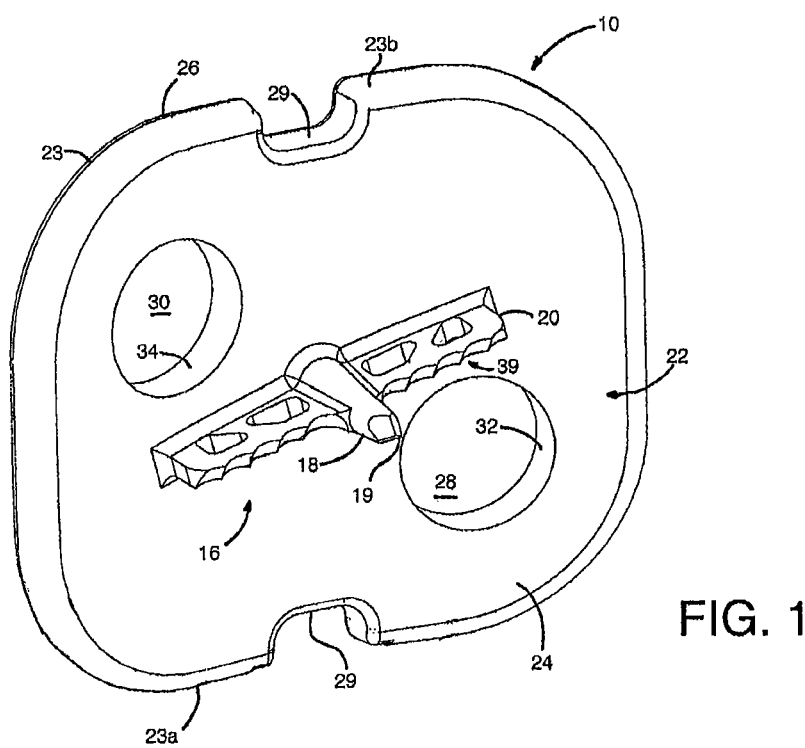
FIG. 1 is a perspective view of a mounting device showing a contoured plate body and a bone securing portion thereof depending from an inferior bone engaging surface of the plate body.

Referring to FIGS. 1-8, there is illustrated an exemplary mounting device 10 that is arranged and configured for being driven in a bone in order to support at least one, and preferably two, anchor members 12 as part of a stabilizing system 14. Preferably, the mounting device 10 is in the form of a vertebral cleat that is configured for being driven in a vertebral bone as part of a bone stabilization system to fix adjacent vertebrae relative to each other. The mounting device 10 includes a bone securing member 16 with at least one elongate spike portion 18 that permits rotation of the mounting device 10 relative to a bone surface when the spike portion 18 is partially driven into the bone so that a surgeon can orient the mounting device 10 into a final position on the bone. The securing member 16 also preferably includes an elongate keel portion 20 extending transverse to the spike 18 that hinders further rotation of the mounting device 10 when the spike portion 18 and the keel portion 20 are both fully driven into the bone. As part of the stabilizing system 14, the mounting device 10 is advantageous because it minimizes toggling of the anchor members 12 that may be experienced when the anchor members 12 are under load.

The mounting device 10 includes a plate body 22 having a generally rectangular shape defined by a perimeter edge 23. Extending between the perimeter edge 23, the plate body 22 includes a lower or inferior surface 24 spaced from an upper or superior surface 26. The perimeter edge 23 further defines a pair of notches 29 that extend inwardly to each of the surfaces 24 and 26 of the base member 22 from opposing sides 23a and 23b of the perimeter edge 23. As further described below, the notches 29 are sized and configured to receive portions of an insertion tool to facilitate insertion of the mounting device 10 to a bone material. The plate body 22, and preferably the inferior surface 24 thereof, has a contour or curvature so that it may mate or engage substantially flush with a surface of the bone when the spike 18 and keel 20 of the device 10 are substantially fully driven therein.

Extending through the plate body 22 is at least one, and preferably two, screw openings or passages 28 and 30 that are defined by interior edges 32 and 34, respectively, of the plate member 22. Preferably, the passages 28 and 30 are located on opposite sides of the securing member 16. Each passage 28 and 30 is sized and configured to receive one of the anchor members 12 therethrough. If desired, the interior edges 32 and 34 may include threading configured to mate with corresponding threading on the anchor members 12.

Figure 2:
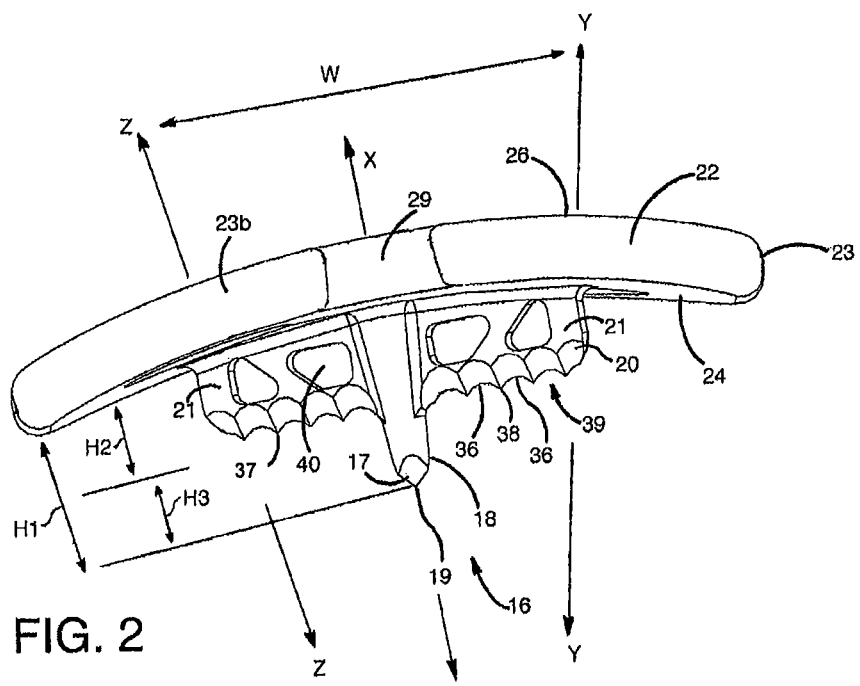
FIG. 2 is an elevational view of the mounting device of FIG. 1 showing a central spike portion and an elongate keel portion with a serrated edge of the bone securing portion.
Figure 3:
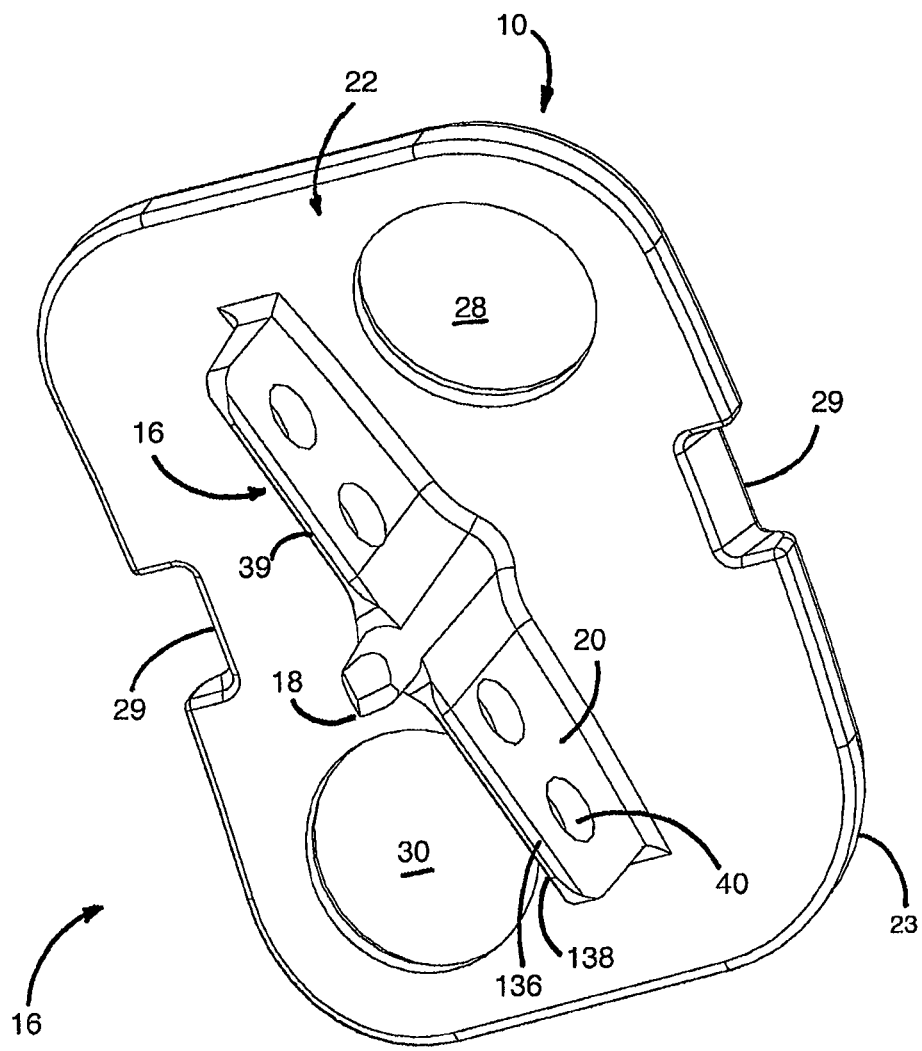
FIG. 3 is a perspective view of a modified mounting device showing an elongate keel with a knife edge.

The spike portion 18 and the keel portion 20 depend from the inferior surface 24 of the plate body 22. In use, the securing member 16 is adapted for securing the mounting device 10 in at least two different configurations on a bone. As suggested above, in a first or partial insertion configuration, the mounting device 10 is pre-positioned on a bone surface, and the spike portion 18 partially driven into the bone so that the plate body 22 may rotate about an axis X extending through the spike 18 (FIG. 2). In this manner, after such initial insertion, a surgeon may rotate the plate body 22 about the axis X so that the passages 28 and 30 of the mounting device 10 can be located proximate and over a desired final location on the bone. Once the passages 28 and 30 are proximate such final location, the spike portion 18 and the keel portion 20 can be substantially fully driven into the bone into a second or full insertion configuration where the inferior surface 24 is in mating engagement with a bone outer surface. In this full insertion configuration, the keel portion 20 driven into the bone material hinders further rotation of the base member 22 about the axis X.

The spike portion 18 is preferably a narrow, elongate member in the form of a cone or cylinder that is positioned at a center portion of the base member inferior surface 24. At a lower end 17 of the spike portion 18, a piercing point 19 is formed to permit the spike to pierce into bone material upon application of an impact force to the mounting device 10 at the opposite, superior surface 26 by an appropriate impact tool. As shown, the spike portion 18 has a larger cross-sectional area adjacent the base member than near the piercing point so that the spike 18 tapers inwardly toward the axis X as it extends downwardly from the inferior surface 24. Such taper permits easier initial insertion of the spike because of the smaller cross-section at the piercing point. While the spike is illustrated as a narrow, elongate cylinder, the spike 18 may also be substantially flattened or have other shapes or sizes, and it may also vary in location on the base member 22.

The elongate keel portion 20 extends along a length of the base member 22 in a direction generally transverse to, and more particularly, generally orthogonal to, the axis X and the spike portion 18. Preferably, the elongate keel portion 20 and spike portion 18 are integrally formed together. A lower edge 37 of the keel portion 20 includes a cutting surface 39 that is configured to be easily driven into bone when an impact force is applied to the mounting device 10 on its superior surface 26. In the embodiment shown in FIGS. 1-2, the cutting surface 39 is a serrated edge formed from a plurality of scalloped portions 36 adjacent each other that combine together to form a sharp edge or point 38. In a modified embodiment shown in FIG. 3, the cutting surface 39 is a straight knife edge formed from an inclined portion 136 of the keel that extends towards a sharp cutting edge 138. The cutting surface 39 in the form of the serrations 36 or knife edge 138 permits the keel 20 to penetrate a bone material when the mounting device 10 is impacted with an appropriate tool.

To permit the mounting device 10 to be partially inserted into the bone where the plate body 22 may be rotated about the axis X, the keel portion 20 and the spike portion 18 have different heights or distances along the axis X. That is, as best shown in FIG. 2, an axial height H1 of the spike portion 18 is longer than an axial height H2 of the keel portion 18 by a distance H3. In this manner, when in the partial insertion configuration, the spike portion 18 may be inserted into the bone any portion of the distance H3 so that the keel portion 20 is not yet inserted into the bone, which permits the rotation of the plate body 22 about the axis X. Such arrangement is advantageous because it permits the surgeon to pre-position the plate body 22 to a proximate location while it is spaced above or over, or only loosely engaged with, the bone, and from this pre-position orient the passages 28 and 30 by rotating the plate body 22 about the axis X into a final position prior to the full insertion of the spike portion 18 and the keel portion 20 into the bone.

To provide a more stable mounting into the bone and further resist anchor member toggling and rotation of a fully inserted device 10, the keel portion 20 includes a relatively large bone contact or surface area 21. This surface area 21 is provided by the keel 20 having a width W and height H2 (FIG. 2) so that it extends along a portion of the base member inferior surface 24. In use, the relatively large surface area 21 of the keel 20 provides increased contact area or confronting surface with bone material to provide enhanced resistance to movement such as toggling or rotation.

To provide further resistance to toggling and rotation, the keel portion 20 also includes at least one, and preferably a plurality, of bone growth windows 40 extending therethrough. In use, after the keel portion 20 is fully inserted into the bone, the bone growth windows 40 are sized and shaped to permit bone material to grow and extend through the keel 20 to provide a more secure attachment of the mounting device 10 to the bone. With bone growth through the keel, the mounting device 10 provides a relatively stable mounting base for the anchor members 12 because the mounting device 10 will be more firmly secured to the bone. As shown in FIG. 2, the bone growth windows 40 have a variety of rectangular or triangular shapes; however, the bone growth windows 40 may also have other shapes, such as the circular shapes as shown in the modified keel 20 in FIG. 3.

Referring to FIGS. 4-8, an exemplary form of the stabilizing system 14, which employs a pair of spaced mounting devices 10, is illustrated in more detail. In such form, the system 14 is adapted for securing adjacent vertebral bones as part of a bone stabilization system. While illustrated in a more horizontal arrangement for clarity, the system 14 is configured for a more vertical insertion between adjacent vertebrae and includes a superior mounting device 10a for being mounted to a superior vertebrae (not shown) and a inferior mounting device 10b for being mounted to a inferior vertebrae (also not shown). To connect and stabilize the vertebrae, the system 14 also includes a pair of elongate members 50, such as spinal rods, extending between the anchor members 12.

More specifically, the system 14 includes a first anchor member 12a extending through a passage 28a of the superior mounting device 10a and a second anchor member 12b extending through a passage 28b of the inferior mounting device 10b. In between the first and second anchor members 12a and 12b, there extends a spinal rod 50a to connect the two anchor members together. Likewise, third and fourth anchor members 12c and 12d extend through passages 30a and 30b, respectively, of the superior and inferior mounting devices 10a and 10b and are connected to a second spinal rod 50b in a similar manner. The spinal rods 50a and 50b are secured to the anchor members 12a, 12b, 12c, and 12d through any suitable securing mechanism, such as clips, caps, and other locking members.

Figure 5:
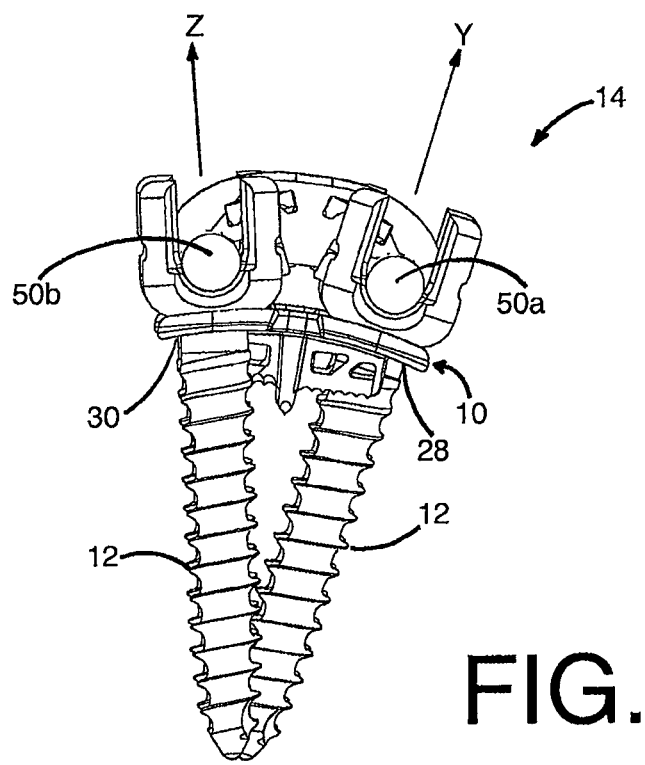
FIG. 5 is an elevational view of the stabilization system of FIG. 4 showing canting of anchor members extending through one of the mounting members.

To provide a more secure attachment to the bone, the two anchor members 12 in each mounting device 10 (i.e., anchor members 12a and 12c in device 10a and anchor members 12b and 12d in device 10b) are canted relative to each other as best illustrated in FIG. 5. In this regard, each passage 28 and 30 has a central axis Y and Z, respectively, therethrough that is canted relative to each other. Preferably the axes Y and Z are canted an amount β, which is preferably about 20° relative to each other. Such canting renders it more difficult for the anchor members 12 and/or the mounting devices 10 to be inadvertently displaced from the bone material to which they are secured, since the transverse angles of the anchor members will resist removal directly along the axis of one or the other anchor member, or along the axis of the securing member of the mounting device.

Figure 6:
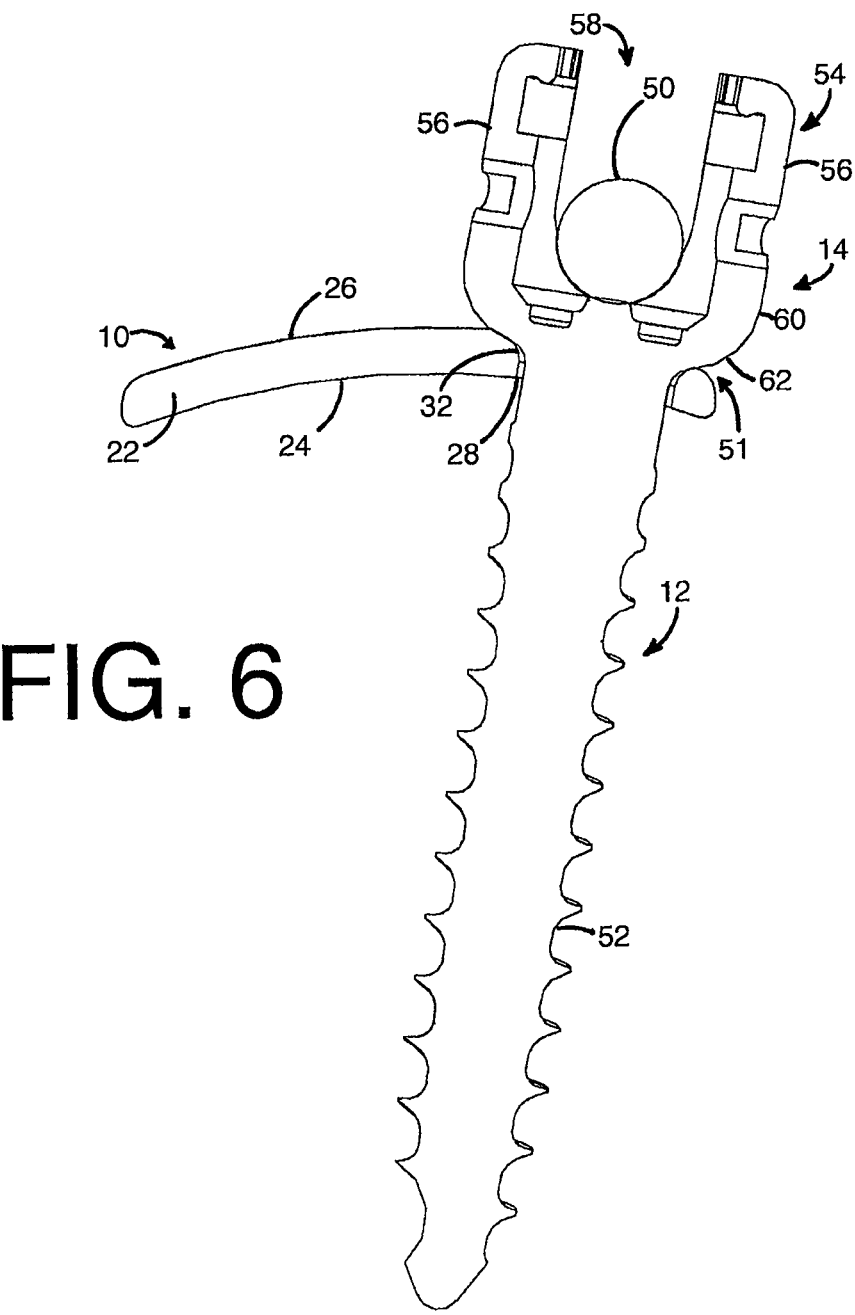
FIG. 6 is a cross-sectional view of the stabilization system of FIG. 4 showing a mating relationship between the anchor member and a through passage in the mounting member.

Referring to FIG. 6, the mounting device 10 preferably receives the anchor member 12 in a mating relationship 51. In an exemplary form, the anchor member 12 includes a narrower, lower screw portion 52 for being screwed into a bone material and an enlarged upper coupling portion 54 for mating with the mounting device 10 and receiving the spinal rod 50. The upper coupling portion 54 is preferably in the form of a yoke having spaced side walls 56 defining an interior space 58 to receive the spinal rod 50 therein and extending therethrough. An outer surface of the yoke side walls 56 includes an upper, generally straight side portion 60 and an intermediate, transition portion 62 that curves between the wider, straight portion 60 and the more narrow screw portion 52.

To form the mating relationship 51, the inner edges 32 and 34 of the base member passages 28 and 30 have a contour that curves outwardly from the passages to the superior surface 26 of the base member to form a generally countersunk recess surrounding each of the passages 28 and 30. This contour substantially matches the curved transition portion 62 of the anchor member 12 to form the mating relationship 51. Within these countersunk recesses, a lower portion of the anchor member coupling portion 54 is seated therein to provide for a more secure coupling between the anchor members 12 and mounting device 10. The countersunk recesses also aid in the proper alignment of the anchor members 12 along the passage axes Y and Z so as to form the desired canting of the anchor members 12. If the anchor members are of a polyaxial variety, comprising for instance a screw pivotable in a connecting member or yoke, the countersunk recesses may be contoured to align and stabilize the connecting member, preventing the connecting member from pivoting with respect to the screw once the connecting member is fully seated in the contoured countersunk recess of the mounting device.

Figure 4:
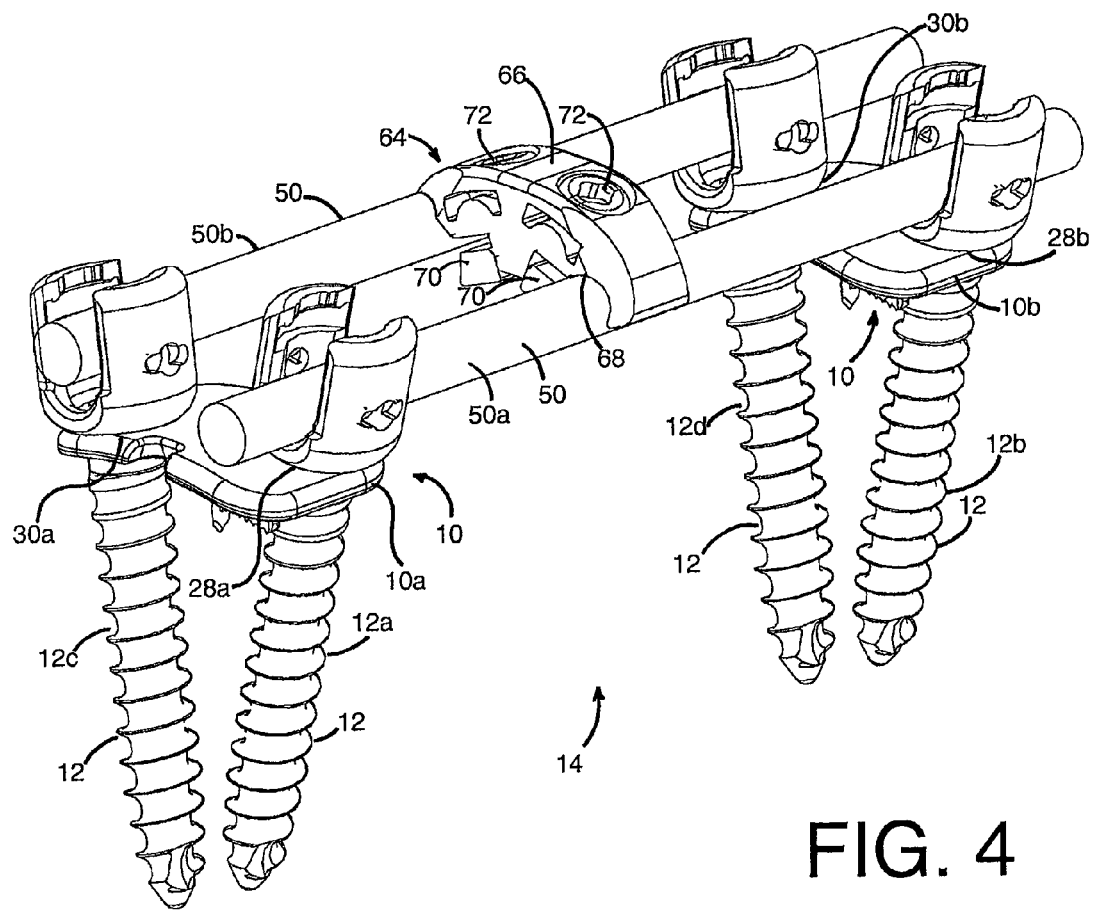
FIG. 4 is a perspective view of a vertebral stabilization system including a pair of spaced mounting members.
Figure 7:
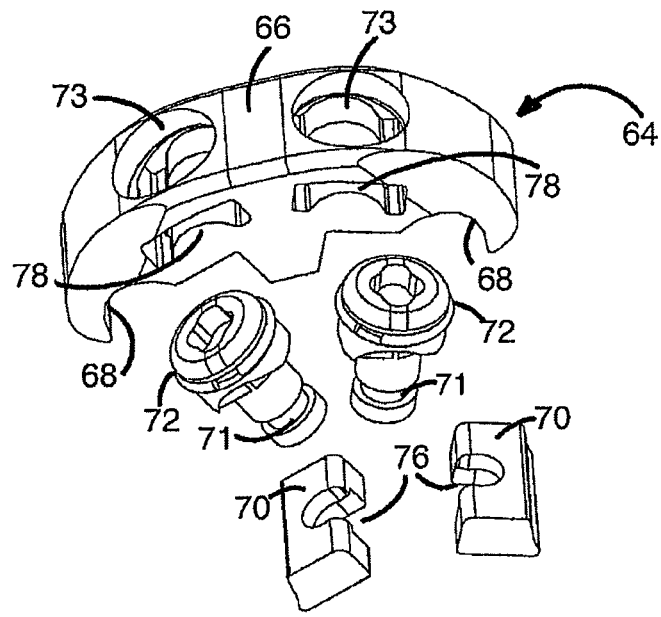
FIG. 7 is a perspective view of an alignment device configured to hold elongate members of the stabilization system of FIG. 4.
Figure 8:
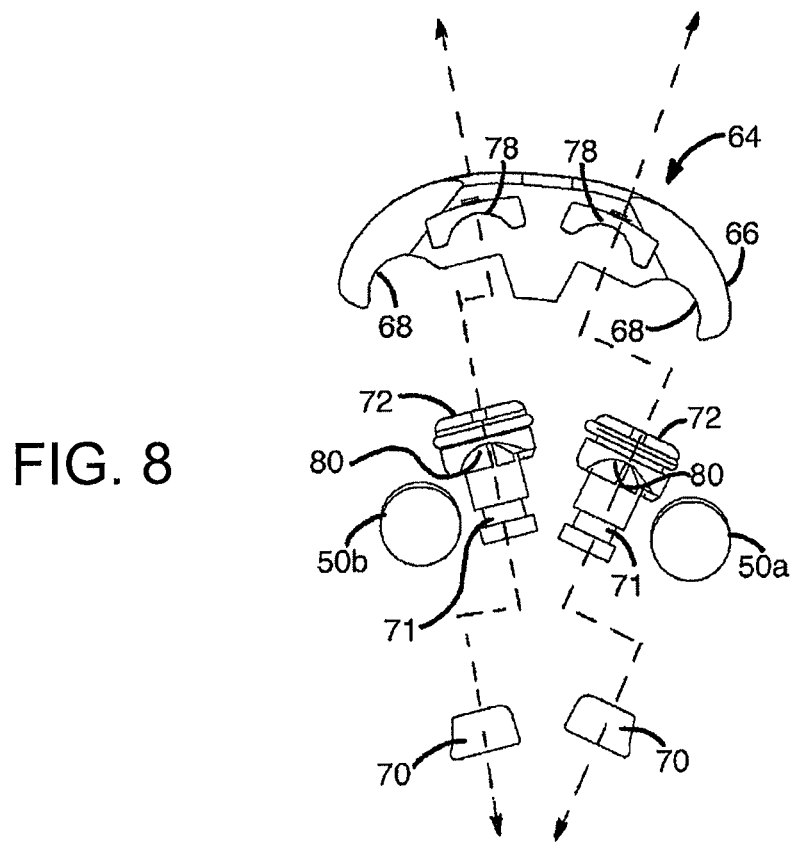
FIG. 8 is an elevational view of the alignment device of FIG. 7 showing a cross-link member, a pair of fasteners, and a pair of wedge blocks.
Figure 9:
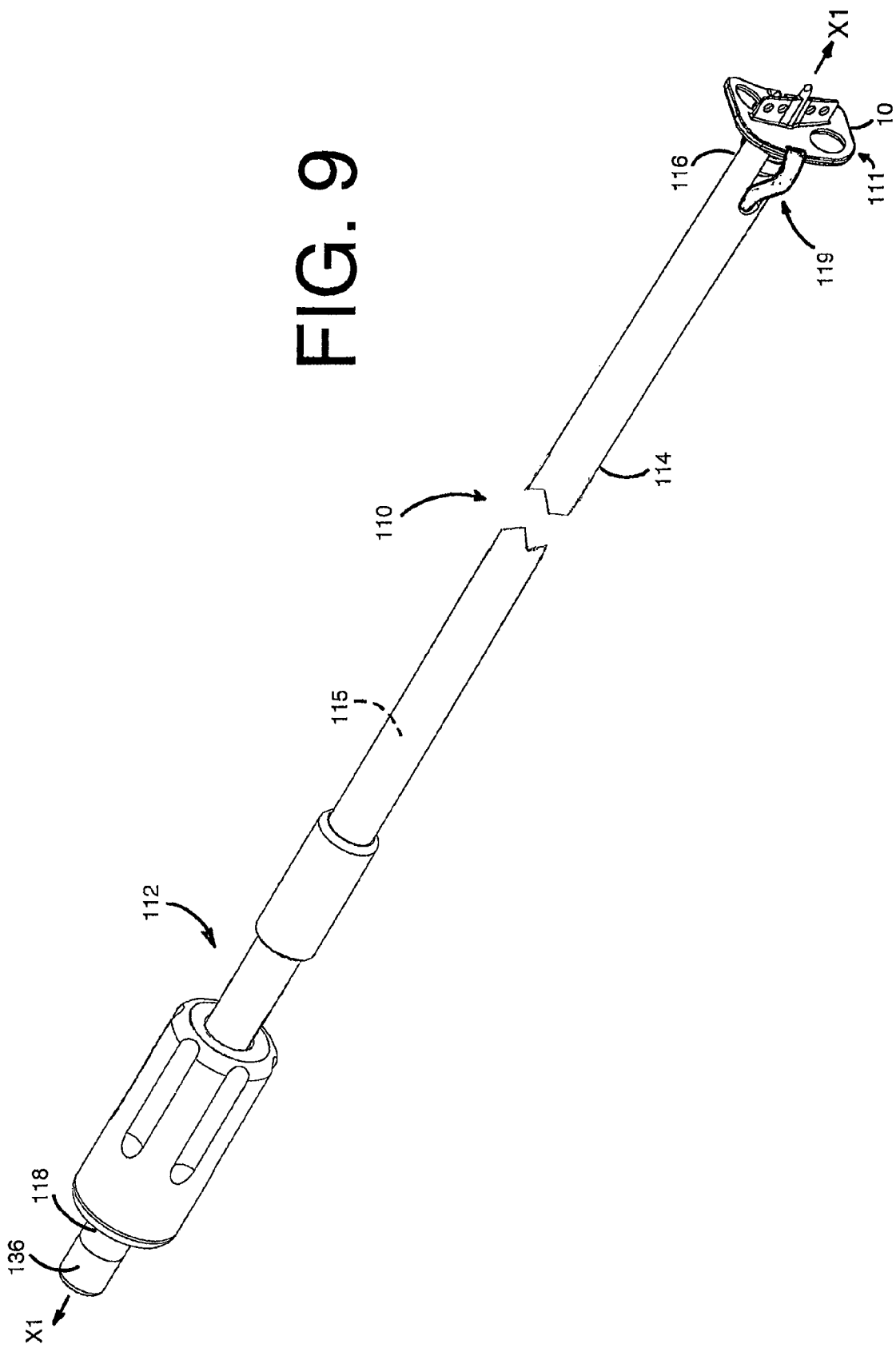
FIG. 9 is a perspective view of an instrument arranged and configured to grasp and release the mounting device for insertion thereof into a bone.
Figure 10:
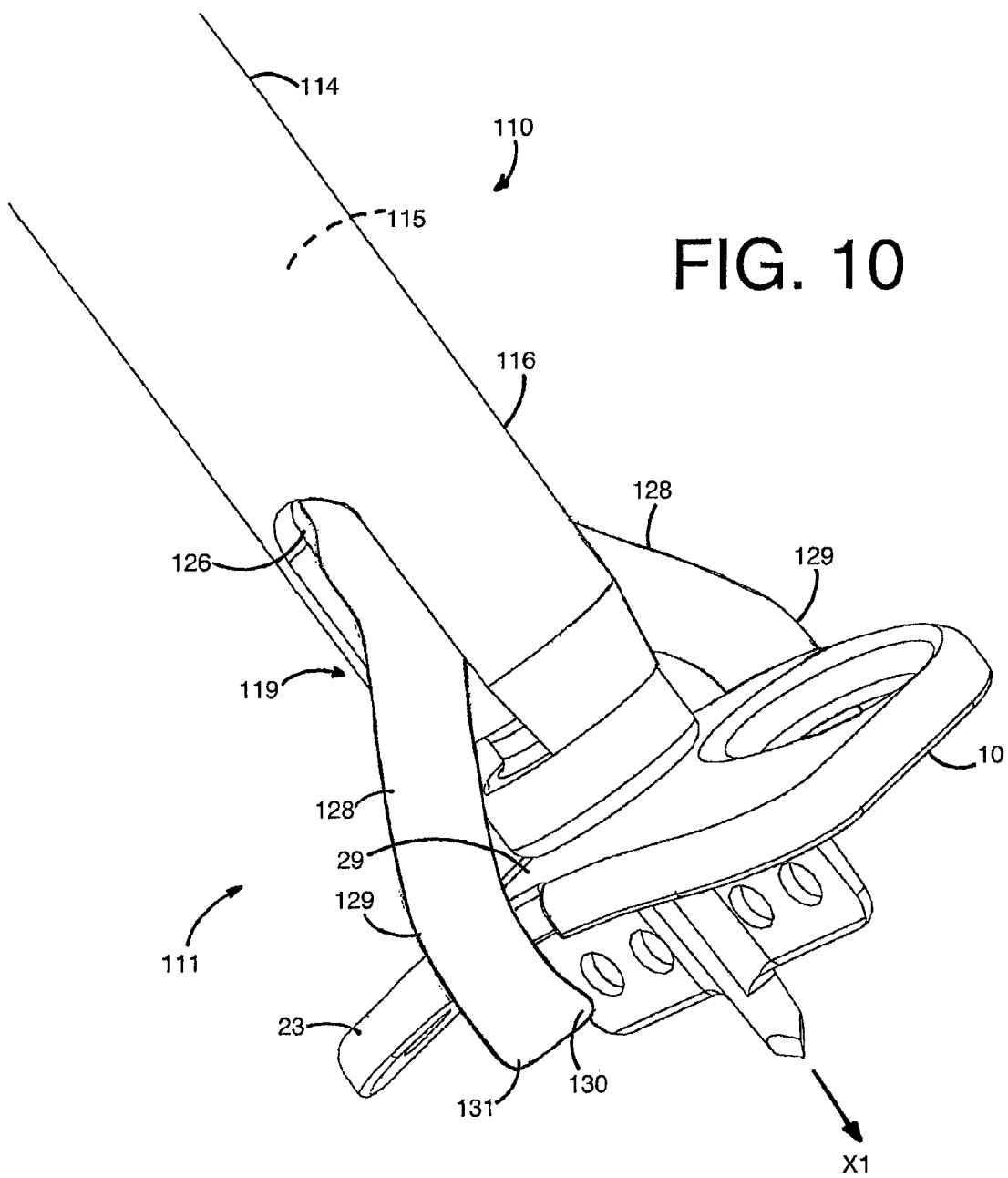
FIG. 10 is a perspective view of an operative end of the instrument of FIG. 9.
Figure 11:
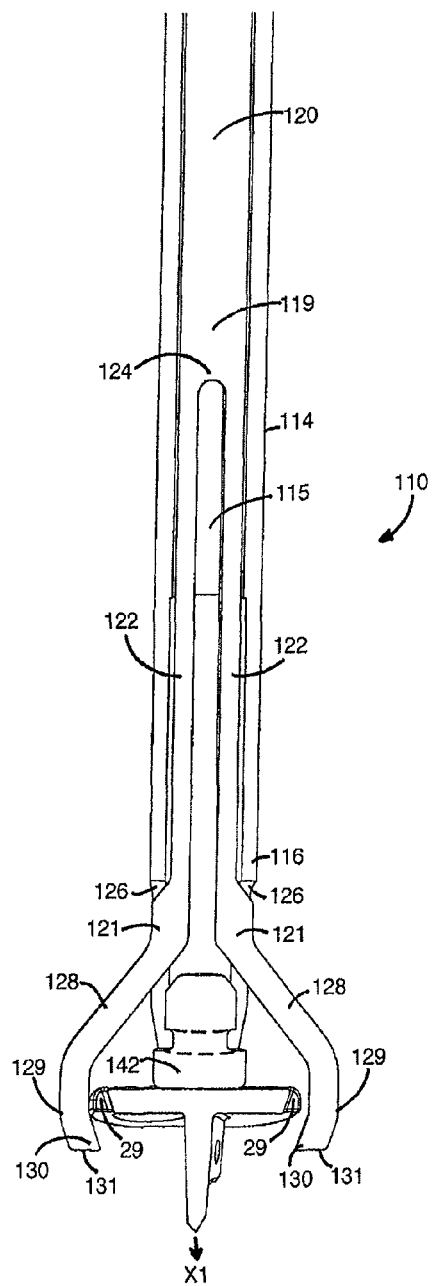
FIG. 11 is a cross-sectional view of the operative end of the instrument of FIG. 9.

Referring to FIGS. 4 and 7-8, to help orient and align the connecting rods 50 within the stabilization system 14, an alignment device 64 may be employed to couple each rod 50a and 50b intermediate the spaced mounting devices 10a and 10b. The alignment device 64 helps hold the rods 50 into a generally parallel relationship and minimizes any relative movement therebetween. The alignment device 64 preferably includes a cross-link member 66 having pocket portions 68 sized and configured to receive at least an upper portion of each rod 50.

To secure the cross-link member 66 to the rods 50, a wedge block 70 is employed under each rod 50 opposite the pocket portions 68 to cam the rods into the pocket portions 68. To tightly secure this assembly, a fastening or cam member 72 extends through passageways 73 in the cross-link member 66 and pulls the wedge block 70 tightly against a lower surface of the rods 50 to wedge the rods 50 into each pocket portion 68. The fastening member 72 is coupled to the wedge blocks 70 via an annular slot 71 in a lower end of the fastener 72 that is received via a friction-fit in a generally U-shaped slot 76 within the wedge block 70. As best illustrated in FIG. 8, in order to tightly wedge the rods 50 into the cross-link member pocket portions 68, the passageway 73 in the cross-link member 66 defines a cam surface 78 that cooperates with a corresponding cam surface 80 on the fastener 72 that pulls the wedge bock 70 towards the rod 50 when the fastener 72 is rotated within the passageway 73. While a preferred assembly of the alignment device 64 is described above, it will be appreciated that the alignment device 64 can include a variety of different forms and components and can be coupled to the rods 50 using a variety of methods.

Turning to FIGS. 9-14, an insertion instrument 110 is illustrated that is adapted and configured to grasp and release the mounting device 10 in order to facilitate the implanting thereof on a vertebral bone in both of the insertion configurations described above. In general, the instrument 110 includes a gripping portion 111 that is configured to hold the mounting device 10 and an actuator portion 112 that is operative to manipulate the gripping portion 111 to grasp and release the mounting device 10 as needed.

More specifically, the instrument 110 includes an elongate sleeve or tube 114 defining a central bore 115 extending therethrough. The gripping portion 111 is on a first or operative end 116 of the sleeve 114, and the actuator portion 112 is on a second or actuating end 118 of the sleeve 114. The sleeve 114 includes a longitudinal axis X1 extending through the central bore 115. An elongate grasping fork 119 is received within the bore 115 and adapted and configured to slide along the longitudinal axis in response to the actuator portion 112.

Figure 15:
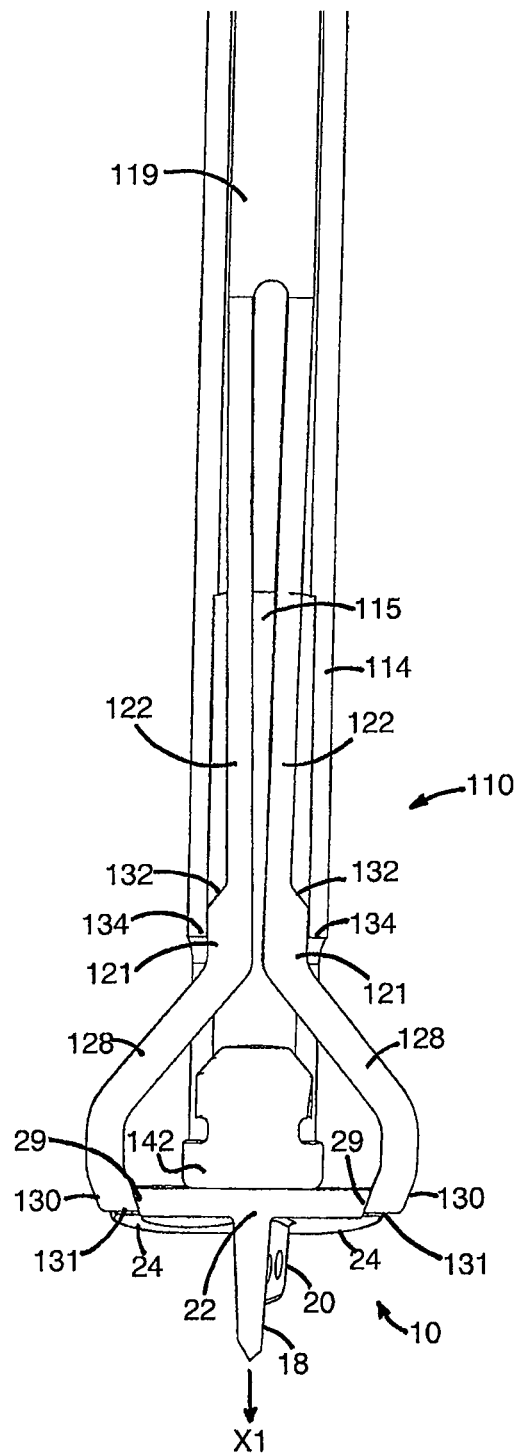
FIG. 15 is a cross-sectional view of the operative end of the instrument shown grasping a mounting device.

Referring to FIGS. 10-12 and 15, the elongate grasping fork 119 includes a shaft portion 120 and spaced resilient arms 122 extending outwardly from a distal end 124 of the shaft portion 120. A portion 121 of each resilient arm 122 extends through U-shaped slots 126 defined on opposing sides of the sleeve 114 at the operative end 116 thereof. The resilient arms 122 flare outwardly from each other and away from the longitudinal axis X1 to form spaced holding forks 128, each of which curves inwardly at an end portion 129 thereof to form a hook portion 130. In use, the hook portions 130 are sized and configured to be received within the notches 29 defined in the perimeter edge 23 of the mounting device 10 when the resilient arms 122 are biased inwardly toward the longitudinal axis X1 by the actuator portion 112 as illustrated in FIG. 15.

Figure 12:
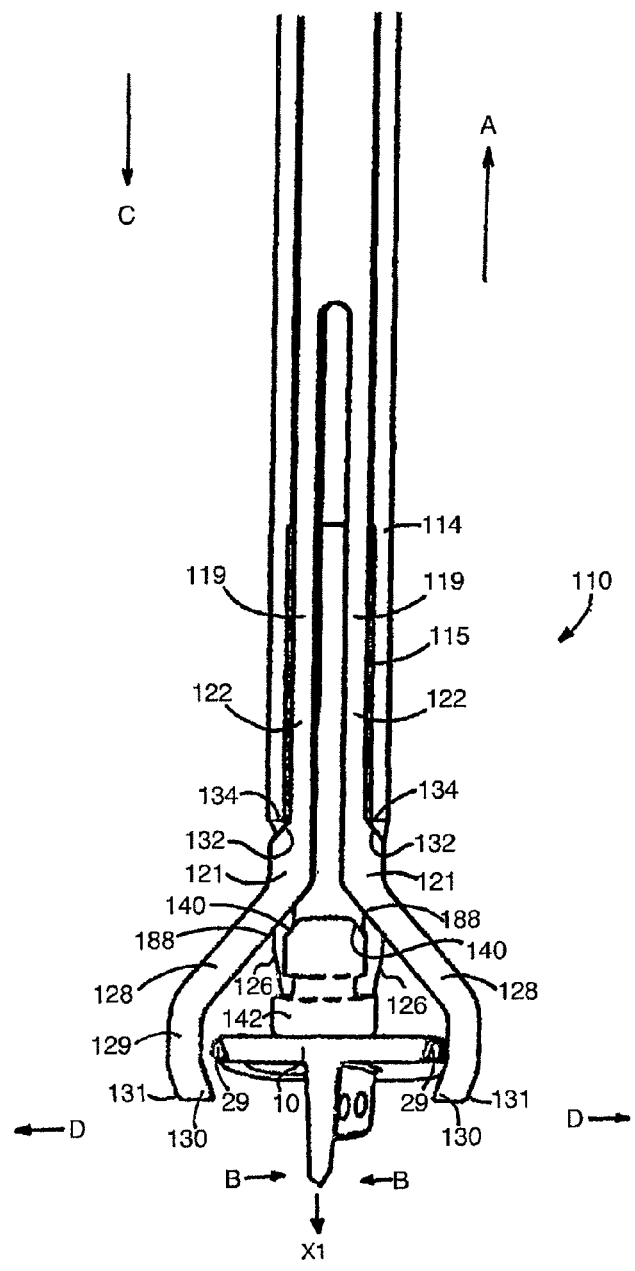
FIG. 12 is a cross-sectional view of the operative end of the instrument of FIG. 9 showing movement of an elongate fork in a grasping direction and a releasing direction.

As illustrated in FIG. 12, in order to grasp the mounting member 10, the elongate fork 119 is drawn into the sleeve 114 in a grasping direction (arrow A) along the longitudinal axis X1. With such motion, ramp surfaces 132 on the portion 121 on each spaced finger 120 that extends through the sleeve slots 126 contacts an inner edge 134 of the sleeve slots 126 to cam the spaced resilient arms 120 inwardly toward the longitudinal axis X1. The inward motion of the resilient arms 120 also causes the spaced holding forks 128 to move towards each other (arrows B) so that the hooked end portions 130 of the forks 128 grasp the outer perimeter edge 23 of the mounting device 10, and specifically, are received within the perimeter notches 29. In this grasping configuration as shown in FIG. 15, distal ends 131 of the hooked end portions are flush, and preferably, spaced inward from the mounting device inferior surface 24. In this manner, the hooked ends 131 will not interfere with the placement of the mounting device 10 on the bone. The tool 110 may then be used to position the grasped mounting device 10 in its desired location on the vertebrae where the instrument 110 is then impacted on an end cap 186 on the actuator portion 118 of the sleeve 114 in order to implant the device 10 into the bone.

Once implanted into the bone, to release the mounting device 10, the elongate fork 119 is slid in the opposite or releasing direction (arrow C) along the longitudinal axis X1. With this opposite motion of the elongate fork 119, inner ramp surfaces 188 of the holding forks 128 contact bevel or inclined surfaces 140 located on a cap 142 positioned on the operative end 116 of the sleeve 114. The contact of the inner ramp surfaces 188 with the inclined surfaces 140 causes the spaced fingers 120 to spread apart or move away from the longitudinal axis X1. In addition, the resiliency of the arms 120 also causes them to spring back towards their original position when the ramp surfaces 132 are no longer contacting the slot edges 134. In this same motion, the holding forks 128 also move away from each other and the longitudinal axis X (arrows D) in order to release the mounting device 10.

Figure 13:
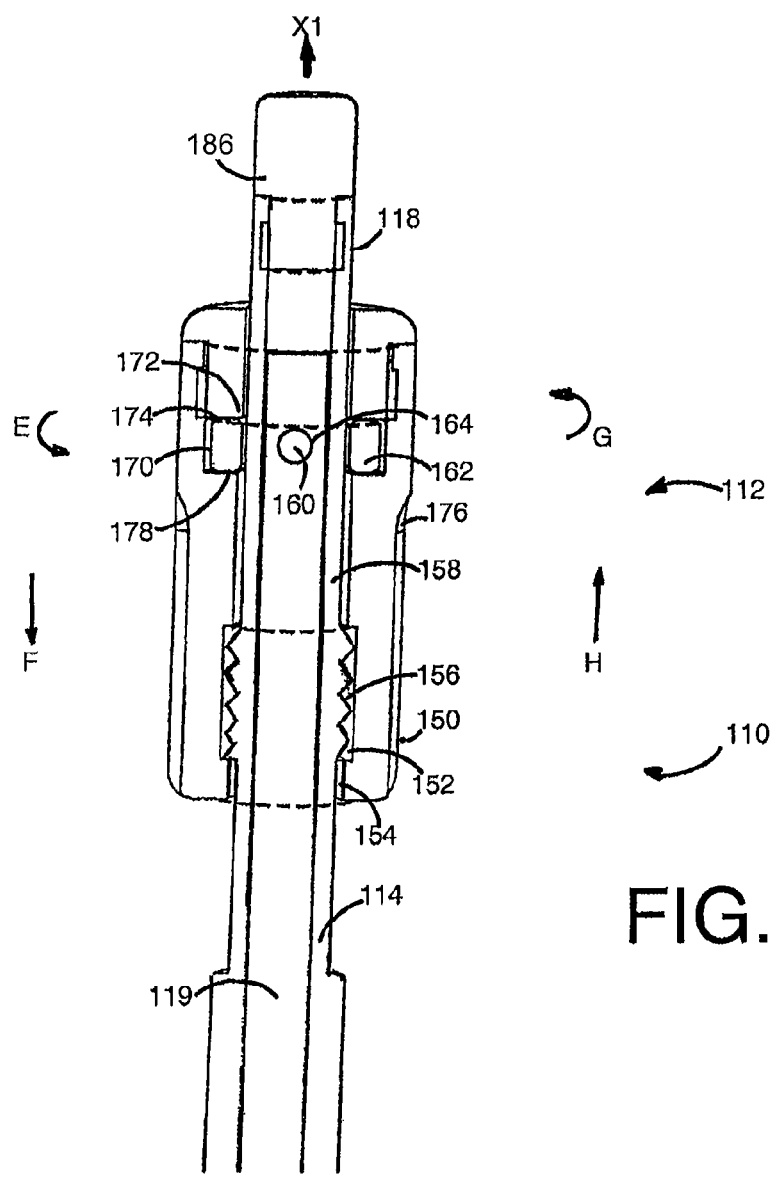
FIG. 13 is a cross-sectional view of an actuator portion of the instrument of FIG. 9.
Figure 14:
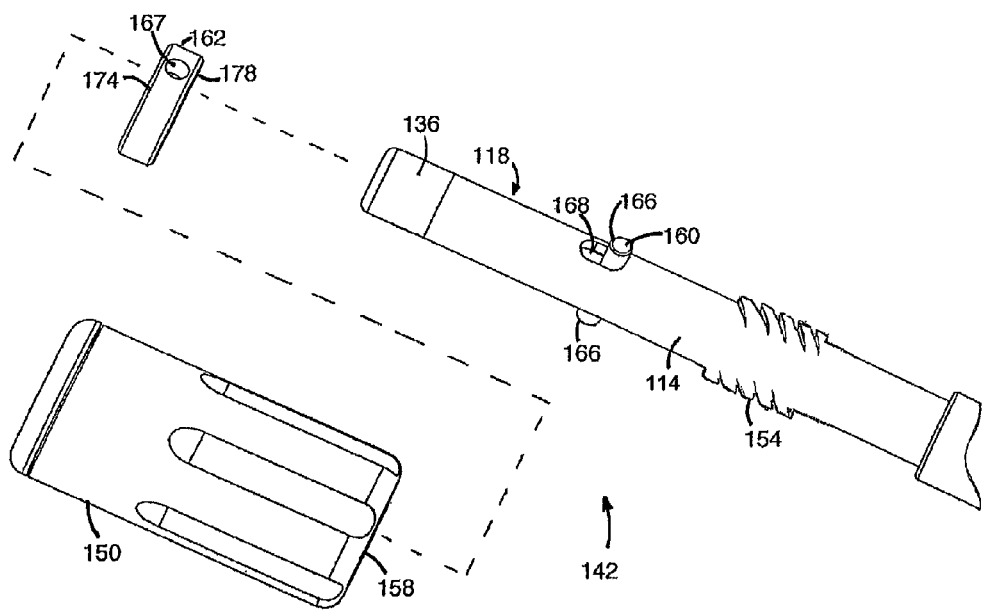
FIG. 14 is an exploded view of the actuator portion showing a handle, a lock pin, and a retaining member.

In order to grasp and release the mounting device 10, the actuator portion 112 is manipulated by a user. That is, the actuator portion 112 is operative to move the elongate fork 119 in the grasping direction (arrow A) and the opposite, releasing direction (arrow C). Referring to FIGS. 13-14, the actuator portion 112 includes a handle 150 that is threadably mated to an outer surface of the sleeve 114 via mating threads 152, which includes external threads 154 on an outer surface of the sleeve 114 and internal threads 156 on an internal surface of a bore 158 that extends through the handle 150. In this manner, the handle 150 can be rotated relative to the sleeve 114 about the longitudinal axis X1 to grasp and release the mounting device 10. That is, the handle 150 is operatively connected to the elongate fork 119 via a lock pin 160 and a retaining member 162 such that rotation of the handle 150 in a first direction slides the elongate fork 119 in the grasping direction and rotation in a second, opposite direction slides the elongate fork 119 in the releasing direction.

More specifically, the lock pin 160 is coupled to the elongate fork 119 by extending through an aperture 164 in an end portion of the elongate fork 119. Opposite ends 166 of the lock pin 160 extend through slots 168 defined in opposing sides of the sleeve 114 such that the lock pin ends 166 protrude through the slots 168. The exposed lock pin ends 166 are coupled to the retaining member 162 by being received in an aperture 167 therein. The retaining member 162 is arranged and configured to slide about the outer surface of the sleeve 114 along the longitudinal axis X1 in response to rotation of the handle 150 about the mating threads 152.

The retaining member 162 is captured within a pocket 170 formed in the handle 150 and slides about the outer surface of the sleeve 114 in response to rotation of the handle 150. For example, upon rotation of the handle 150 in one direction (arrow E), an upper interference surface 172 of the handle pocket 170 contacts an upper surface 174 of the retaining member 162 to push the retaining member 162 along the longitudinal axis X1 in the releasing direction (arrow F). Because the elongate fork 119 is coupled to the retaining member 162 via the lock pin 160, movement of the retaining member 162 in the releasing direction by the handle 150 also moves the lock pin 160 within the slot 168 to move the elongate fork 119 in the same direction. To grasp the mounting device 10, the handle 150 is rotated in an opposite direction (arrow G), and a lower interference surface 176 of the handle 150 contacts a lower surface 178 of the retaining member 162 to slide the retaining member 162 in the grasping direction (arrow H). Because the retaining member 162 is coupled to the elongate fork 119 via the lock pin 160, movement of the retaining member 162 in the grasping direction by the handle 150 also slides the elongate fork 119 in the same direction along the longitudinal axis X1.

In use, a surgeon will grasp the mounting device 10 through the operative end 116 of the instrument 110 as described above and then preposition the piercing point 19 of the mounting device 10 at a desired location on a vertebral bone. An appropriate impact tool (not shown) is then used to impact the end cap 136 on the instrument 110 to partially drive the spike 18 into the bone a portion of the axial distance L3 (FIG. 2) such that the plate body 22 of the mounting device 10 may be rotated about the mounting device axis X to orient the mounting device passages 28 and 30 in a desired location. Once the passages 28 and 30 are properly positioned via rotation of the plate body 22 about the device axis X, the surgeon again impacts the end cap 136 with an appropriate tool to substantially fully drive the remaining portions of the spike 18 and the keel 20 into the bone to substantially complete the insertion of the mounting device 10.

Figure 16:
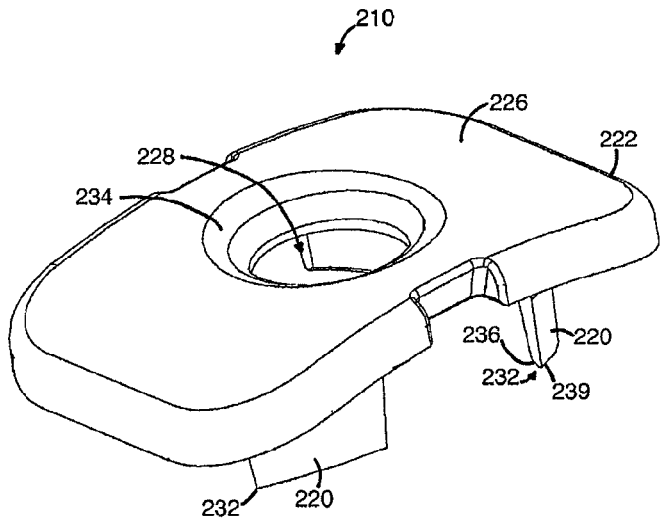
FIG. 16 is a perspective view of a mounting device with a single opening for a fixation device and four keels projecting from the inferior surface of the mounting device and spaced around the perimeter of the opening.
Figure 17:
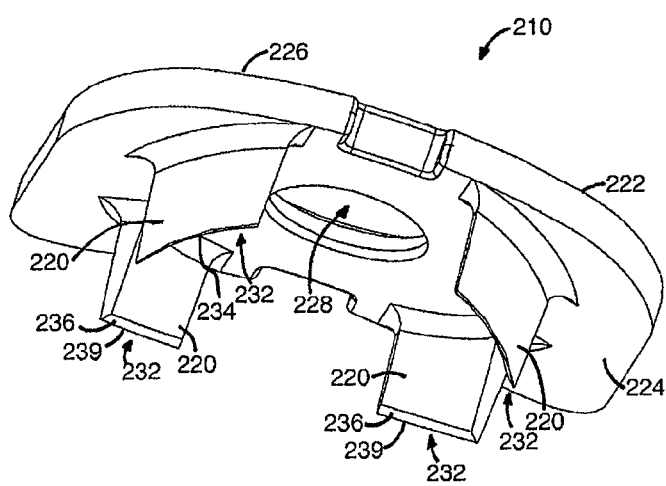
FIG. 17 is a perspective view of the inferior surface of the mounting device of FIG. 16.
Figure 18:
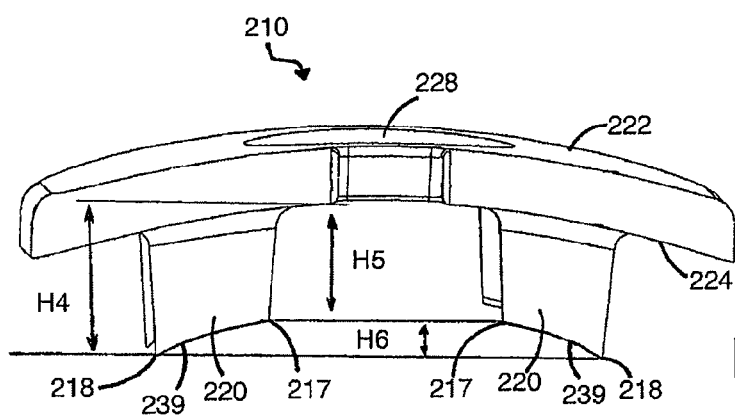
FIG. 18 is a side view of the mounting device of FIG. 16, showing the configuration of the cutting edges of the elongate keels.

Another embodiment of a mounting device 210 is illustrated in FIGS. 16-18. The depicted embodiment receives a single anchor member in a central passage 228, although it is contemplated that the passage may be located elsewhere on the plate body 222 and/or that additional passages may be provided to receive additional anchor members. The mounting device 210 contains four elongate keel portions 220 arranged on the plate body 222 around the central passage 228. The keels have more surface area than narrow spikes of prior art devices, and therefore better resist migration through bone.

A lower edge 232 of each keel portion 220 includes a cutting surface 239 that is configured to be easily driven into bone when the mounting device 210 is impacted on its superior surface 226. In the embodiment shown in FIGS. 16-18, the cutting surface 239 is a straight knife edge formed from an inclined portion 236 of the keel that extends towards a sharp cutting edge 239. The cutting surface 239 may also form a serrated edge. The cutting surface 239 permits the keel 220 to penetrate a bone material when an impact force is applied to the mounting device 210 with an appropriate tool.

To permit the mounting device 210 to be partially inserted into the bone without driving the entire cutting surfaces 239 into the bone, the lower edge 232 is formed as a curve or incline with respect to the plate body 222. That is, as best shown in FIG. 18, a height H4 of a leading projection portion 218 of each keel 220 from the inferior surface 224 of the mounting device 210 is greater than a height H5 of the shortest keel portion 217 from the inferior surface 224 by a distance H6. Although two or more keels including leading portions 218 of the same height may prevent pivoting in the partial insertion stage when the device is inserted straight into the vertebra, such an arrangement is still advantageous because it permits the surgeon to pre-position the plate body 222 to a proximate location on the bone without cutting into the bone with the full length of cutting edge 239. If repositioning is determined to be necessary, minimal damage will have been incurred on the vertebral surface. The mounting device may also be tilted slightly so as to initially contact the vertebra with only one leading portion. When fully inserted, the broad surface areas of the keels 220 provide more stability than spikes of prior mounting plates.

To provide further resistance to toggling and rotation, the keel portions 220 may also include one or more bone growth windows extending therethrough. The large surface area of the keels allows for relatively large windows for bone growth, which will then provide increased resistance to loosening or migration of the device. The leading portions of the keels are located toward the midline of the device, as best shown in FIG. 17, in order to aid in accurate insertion and reduce the chance of slipping or misalignment as the keels 220 are inserted into the bone.

Figure 19:
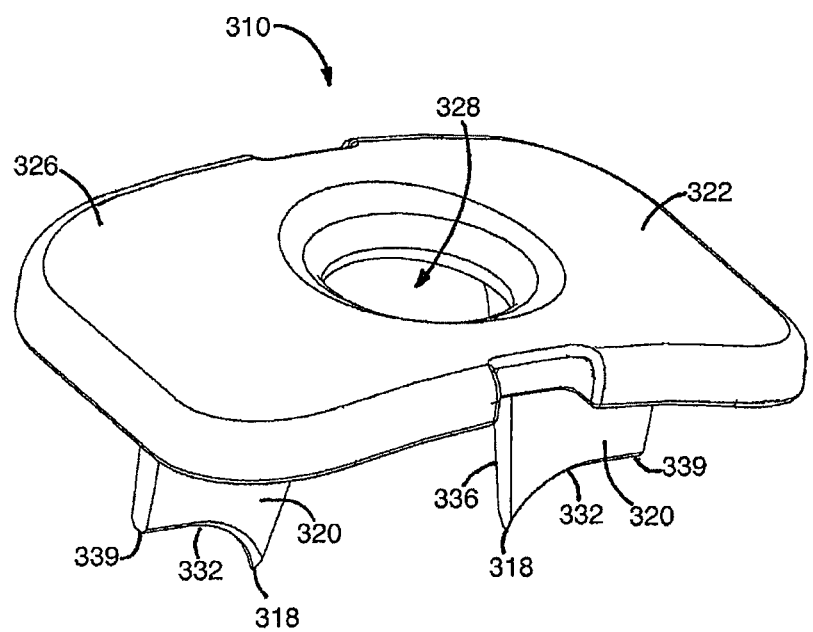
FIG. 19 is a perspective view of another mounting device having two diametrically opposed keels.
Figure 20:
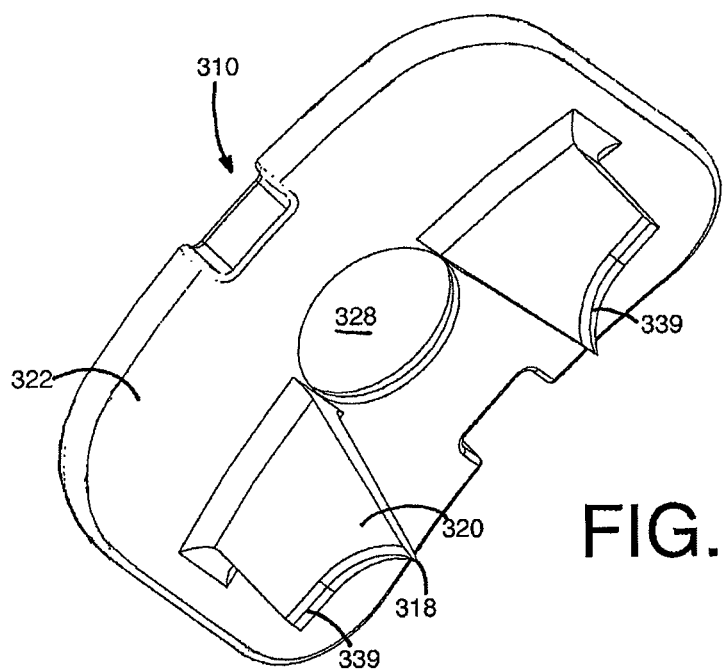
FIG. 20 is a perspective view of the inferior surface of the mounting device of FIG. 19.

Another embodiment of a mounting device 310 is illustrated in FIGS. 19-20. The depicted embodiment receives a single anchor member in passage 328, although it is contemplated that additional passages may be provided to receive additional anchor members. The mounting device 310 contains two diametrically opposed elongate keel portions 320 arranged lengthwise on the plate body 322.

As with the other embodiments, a lower edge 332 of each keel portion 320 includes a cutting surface 339 that is configured to be easily driven into bone when the mounting device 310 is impacted on its superior surface 326. In the embodiment shown in FIGS. 19-20, the cutting surface 339 is a straight knife edge formed from two inclined portion 336 of the keel. The cutting surface 339 may also form a serrated edge. A leading projection portion 318 forms a spike or tooth-like projection extending from the main portion of the keel 320. The height of the leading portion 318 of each keel 320 is greater than a height of the remainder of the keel 320. The keel portions 320 may also include one or more bone growth windows extending therethrough.

Figure 21:
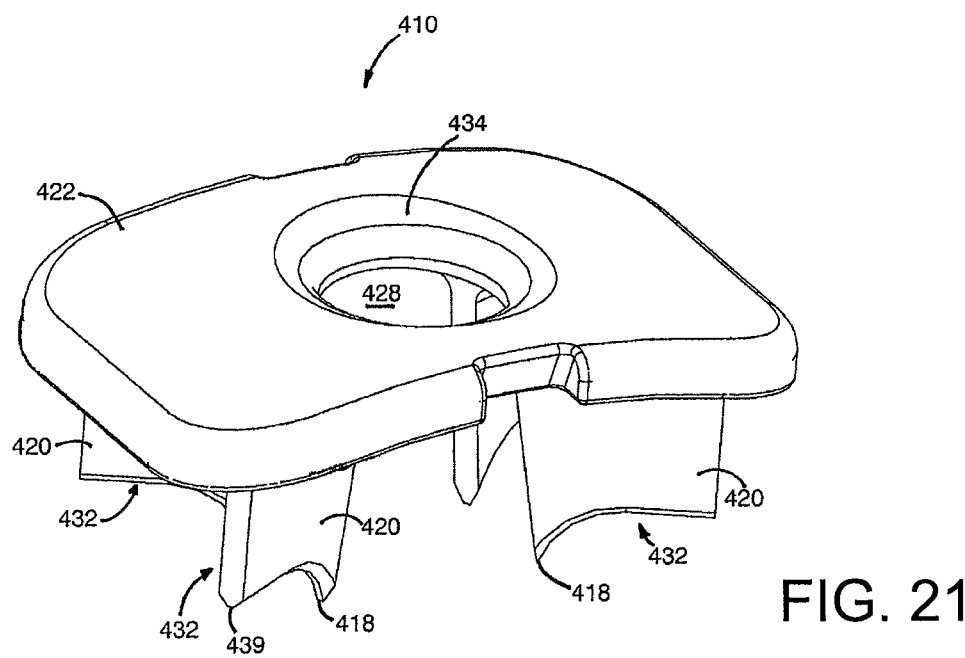
FIG. 21 is a perspective view of another mounting device having four keels aligned radially with respect to a central opening.
Figure 22:
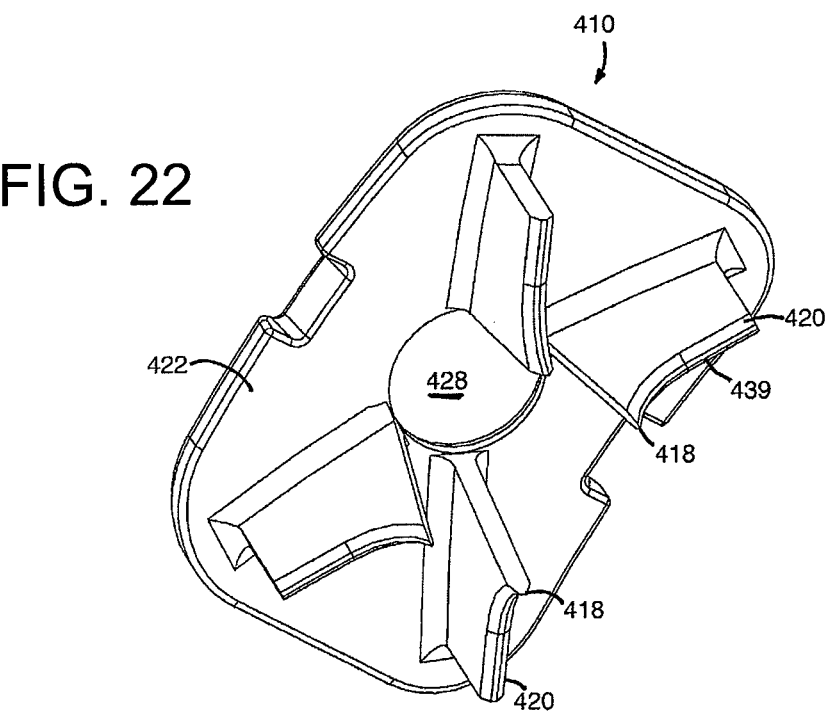
FIG. 22 is a perspective view of the mounting device of FIG. 21.

Another embodiment of a mounting device 410 is illustrated in FIGS. 21-22, which is similar to the device 310 shown in FIGS. 19-20 except that it includes four keels 420 positioned on the plate body 422 so that they extend radially from the central passage 428. The lower edge 432 of each keel portion 420 includes a cutting surface 439. In the version shown, the pointed projections 418 are located adjacent the passage 428.

Figure 23:
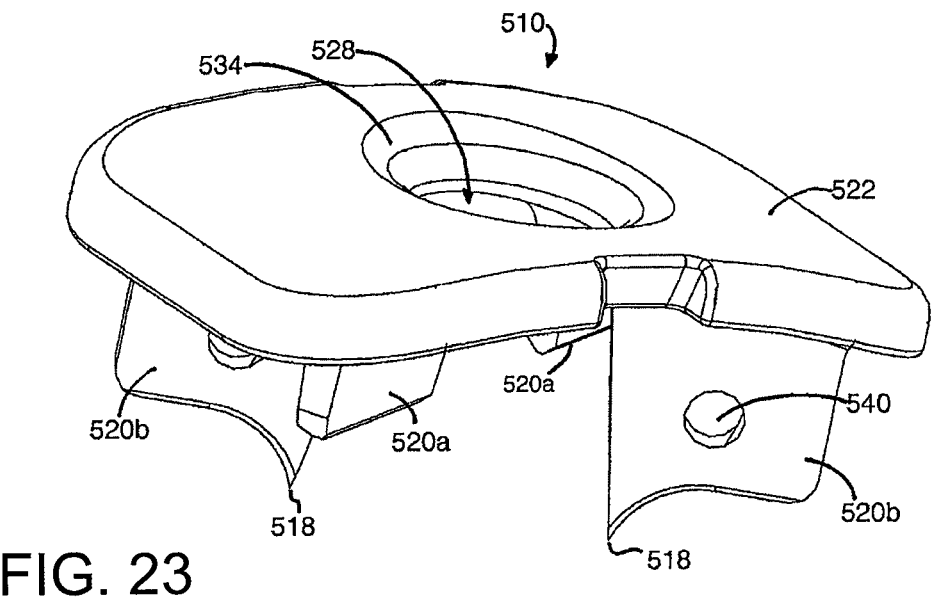
FIG. 23 is a perspective view of another mounting device having two elongate keels with projection portions and two elongate keels without projection portions. Two of the keels have openings to allow bone growth therethrough.
Figure 24:
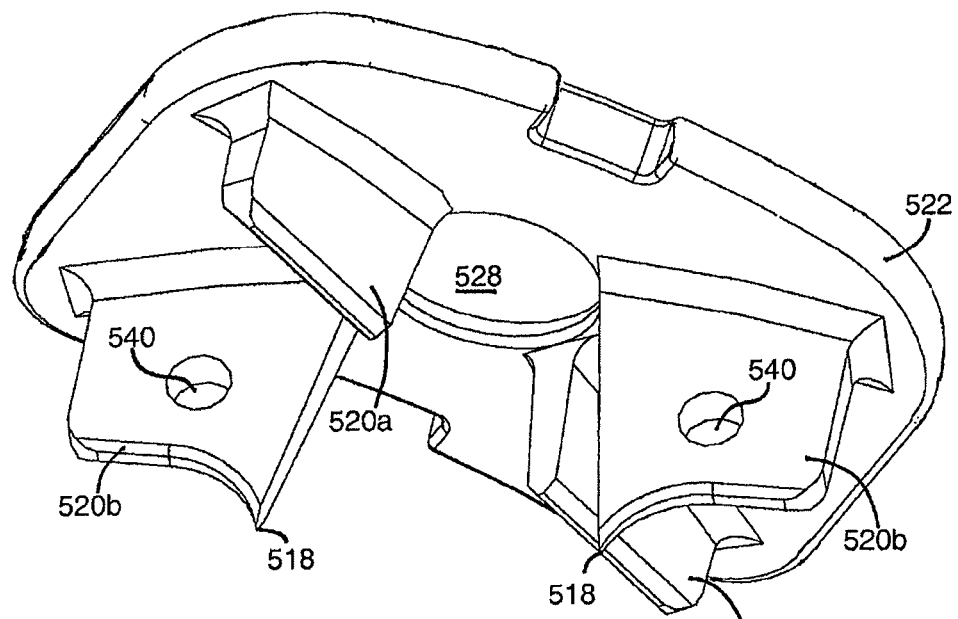
FIG. 24 is a perspective view of the inferior surface of the mounting device in FIG. 23.

Yet another embodiment of a mounting device 510 is illustrated in FIGS. 23-24. In this embodiment, two different configurations of keels 520a and 520b extend from the plate body 522. The taller keels 520b include a leading edge forming a spike or tooth-like projection 518 on the end proximate to the passage 528 for partial insertion of the larger keels 520b prior to full mounting of the device 510. In the partial-insertion stage, the shorter keels 520a do not necessarily cut into the vertebral surface. After full insertion, both the taller keels 520b and the shorter keels 520a will be fully inserted into a vertebra. In the embodiment shown, taller keels 520b each contain an opening 540 to allow for bone growth therethrough. The taller keels 520b are also diametrically opposed from one another across the passage 528, and each is also adjacent shorter keels 520a that are diametrically opposed from one another, although other configurations are also possible.

Figure 25:
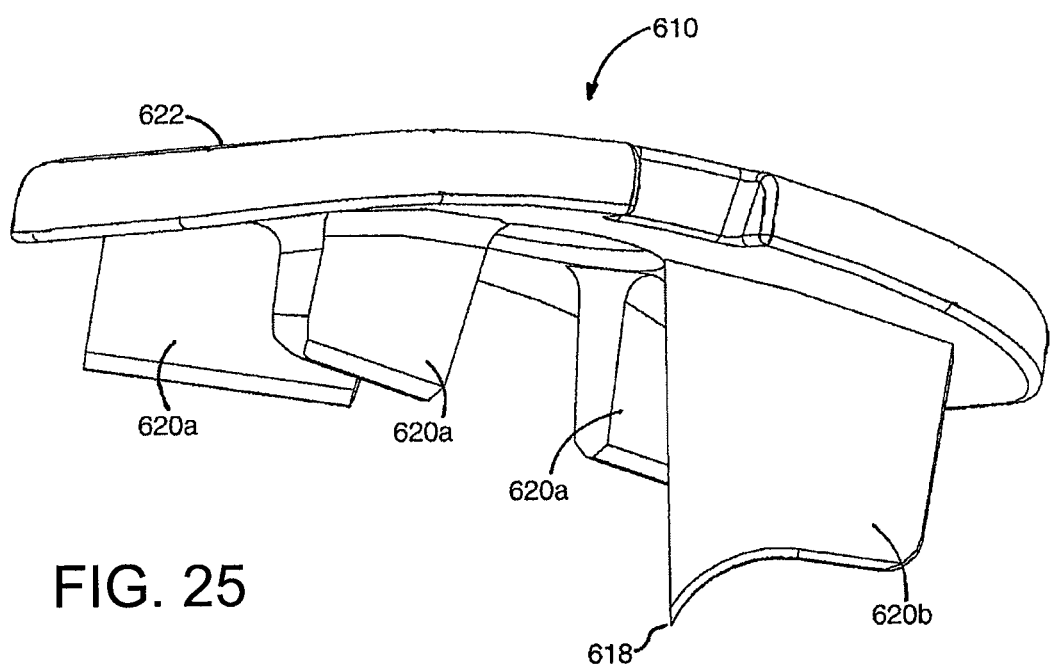
FIG. 25 is a perspective view of another mounting device with for elongate keels, only one of which has a projection portion.

Another embodiment of a mounting device 610 is shown in FIG. 25, which is similar to the device 510 from FIGS. 23-24 except that only one tall keel 620b is provided. The lone leading projection portion 618 of the tall keel 620b may be provisionally inserted into a vertebra so that the device 610 may be pivoted about the spike or projection portion 618 before final positioning and insertion, where the shorter keels 620a are inserted into the bone.

A stabilizing system may incorporate one or more different types of mounting devices as desired.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A vertebral cleat for being secured to vertebral bone, the vertebral cleat comprising:
   a base member having a superior surface and an inferior surface;
   a hole extending through the base member for receiving an anchor member therethrough;
   an elongate keel portion connected to and extending from the inferior surface of the base member and having a cutting edge thereon;
   a projection portion integral to the elongate keel and extending from the inferior surface of the base member in an axial direction and centrally relative to the elongate keel, the projection portion having a base end connected to the base member inferior surface and a tip end extending past the cutting edge of the keel portion and configured to penetrate the bone prior to the elongate keel portion to allow the base member to be rotated thereabout after penetration of the tip end of the projection portion for positioning of the base member hole in a desired location relative to the bone;
   the cutting edge of the elongate keel having either a serrated or knife edge configuration that is the same on either side of the projection portion for penetrating the bone when an impact force is applied to the base member superior surface;
   opposite side surfaces of the elongate keel portion, with the elongate keel portion having a thickness between the opposite side surfaces that is narrower than the base end of the projection portion; and
   a curved surface of the projection portion extending thereabout tapering in the axial direction and sized so that the projection portion extends beyond the keel side surfaces from the cutting edge of the keel portion to the projection base end.

2. The vertebral cleat of claim 1, wherein the elongate keel portion defines at least one window extending therethrough that allows bone growth through the elongate keel portion when implanted in a vertebral bone.

3. The vertebral cleat of claim 1, further comprising a second hole extending through the base member and wherein a central axis of the hole and a central axis of the second hole are canted relative to each other.

4. The vertebral cleat of claim 1, further comprising a recess defined in a perimeter edge of the base member, the recess sized and configured to receive a portion of an insertion tool.

5. The vertebral cleat of claim 1, wherein the base member has a curvature such that the inferior surface conforms to a bone surface.

6. A vertebral support system comprising:
   first and second spaced vertebral cleats each comprising a base member with an inferior surface and a superior surface and having a perimeter edge extending therearound, a pair of openings extending through the base member, an elongate keel having a cutting edge thereon depending from the base member inferior surface and extending therealong and having opposite ends arranged such that the keel at the opposite ends thereof does not extend beyond the openings toward the perimeter edge, and a spike depending from the base member inferior surface and integral to the elongate keel, the spike having a height that is greater than a height of the elongate keel;

a pair of anchor members with one of the anchors members extending through one of the openings in the first vertebral cleat and the other anchor member extending through one of the openings in the second vertebral cleat; and an elongate member extending between the pair of spaced vertebral cleats, the elongate member having one end coupled to the one anchoring member and an opposite end coupled to the other anchoring member.

7. The vertebral support system of claim 6 further comprising a coupling member for receipt of the elongate member extending therethrough, the coupling member secured to one of the base members by an associated anchor member extending through one of the openings in the base member; and a recessed portion of each of the openings of the base member configured for seating a lower portion of the coupling member therein.

8. The vertebral support system of claim 6, further comprising a second pair of anchor members with one of the second pair of anchor members extending through the other one of the openings in the first vertebral cleat and the other of the second pair of anchor members extending through the other one of the openings in the second vertebral cleat; and a second elongate member extending between the first and second spaced vertebral cleats, the second elongate member having one end coupled to the one anchor member of the second pair of anchoring members and an opposite end coupled to the other anchor member of the second pair of anchoring members.

9. The vertebral support system of claim 8, further comprising an alignment device positioned between the first and second vertebral cleats, the alignment device coupled to the elongate member and the second elongate member.

* * * * *